(12) United States Patent
Klose et al.

(10) Patent No.: US 10,605,742 B2
(45) Date of Patent: Mar. 31, 2020

(54) SYSTEM, METHOD AND COMPUTER-ACCESSIBLE MEDIUM FOR PROVIDING BODY-CONFORMING ANIMAL BED, CALIBRATION CELL AND ORGAN PROBABILITY MAP FOR QUANTITATIVE OPTICAL IMAGING OF ANATOMICAL STRUCTURES

(71) Applicants: Alexander Klose, New York, NY (US); Neal Paragas, New York, NY (US)

(72) Inventors: Alexander Klose, New York, NY (US); Neal Paragas, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1521 days.

(21) Appl. No.: 14/319,504

(22) Filed: Jun. 30, 2014

(65) Prior Publication Data

US 2015/0012224 A1 Jan. 8, 2015

Related U.S. Application Data (60) Provisional application No. 61/840,634, filed on Jun. 28, 2013.

(51) Int. Cl.
| | | |
|---|---|---|
| *G01N 21/84* | (2006.01) | |
| *G01N 21/76* | (2006.01) | |
| *G06T 7/00* | (2017.01) | |
| *G01N 21/01* | (2006.01) | |

(52) U.S. Cl.
CPC .......... *G01N 21/84* (2013.01); *G01N 21/763* (2013.01); *G06T 7/0014* (2013.01); *G01N 2021/0181* (2013.01); *G06T 2207/10012* (2013.01); *G06T 2207/10072* (2013.01)

(58) Field of Classification Search
None
See application file for complete search history.

(56) References Cited

U.S. PATENT DOCUMENTS

2012/0017842 A1 1/2012 Yamada et al.

OTHER PUBLICATIONS

Kuo, Chaincy, et al. "Three-dimensional reconstruction of in vivo bioluminescent sources based on multispectral imaging." Journal of biomedical optics 12.2 (2007): 024007.*
Non-final Office action dated Apr. 26, 2019 for U.S. Appl. No. 15/621,983, filed Jun. 13, 2017.
(Continued)

*Primary Examiner* — G Steven Vanni
(74) *Attorney, Agent, or Firm* — Hunton AK LLP (57) ABSTRACT

Exemplary systems, methods and computer accessible mediums which can determine quantitative information of a tissue(s) can be provided, which can include receiving optical information regarding the tissue(s), and determining the quantitative information of the tissue(s), in real time and during the receipt of the optical information, using an atlas. The tissue(s) can be part of a mouse, and the quantitative information can be an in-vivo count of cells or bacteria in the tissue(s). The quantitative information can be determined by co-registering the in-vivo count to the atlas. The optical information can be generated using a mirror gantry(s) so as to simultaneously image at least two opposing views of the tissue(s).

22 Claims, 5 Drawing Sheets

(56) References Cited

OTHER PUBLICATIONS

Klose et al., 2018, Nature Communications, 9: 4262, 12 pages (Year: 2018) Cited in Non-Final Office Action dated Apr. 26, 2019.
Hillman et al, 2007 Nat. Photonics 1:526-530, (Year:2007) Cited in Non-Final Office Action dated Apr. 26, 2019.

* cited by examiner

SYSTEM, METHOD AND COMPUTER-ACCESSIBLE MEDIUM FOR PROVIDING BODY-CONFORMING ANIMAL BED, CALIBRATION CELL AND ORGAN PROBABILITY MAP FOR QUANTITATIVE OPTICAL IMAGING OF ANATOMICAL STRUCTURES

CROSS-REFERENCE TO RELATED APPLICATIONS

This application relates to and claims priority from U.S. Patent Application No. 61/840,634, filed on Jun. 28 22, 2013, the entire disclosure of which is incorporated herein by reference.

FIELD OF THE DISCLOSURE

The present disclosure relates generally to optical imaging of anatomical structures, and more specifically, real time quantitative optical imaging of anatomical structures (e.g., including small animals).

BACKGROUND INFORMATION

Bacterial infections are a leading cause of death worldwide even with the many powerful antibiotics available. The number of antibiotic resistant strains has been increasing, and thus, there is an urgent public health need to validate new antibacterial agents. Testing of new agents in a living mouse can be the most accurate way to track organ burden over time. However, serial plating of organs can be limited to a single point in time per animal tested. Bioluminescent imaging ("BLI") has been shown to be able to qualitatively tract bacterial infection, but it has never been shown to accurately quantify bacterial colony forming units ("CFUs") in 3D in real time.

Cancer is the second leading cause of death in the United States, but survival is gradually improving due to increasingly sophisticated combinatorial therapies which can include chemotherapy, surgery and radiation. In order to continue the development and optimization of new combinatorial treatment strategies, it can be important to have preclinical studies that can accurately model human cancers and their treatment strategies. Immunotherapy has also rapidly become a promising treatment for cancer. While, BLI has been shown to tract bacterial infections, it cannot quantify or tract immune or cancer cells, in real time, and it cannot monitor the tumor size in response to the therapy. Stem cell research has been shown to aid in the repair of damaged tissue; however, there currently is no tool which can monitor the repair process in the living animal.

In vivo imaging of optical reporters in mice, and other small animals, can provide important information regarding the progression of disease states. For example, cancerous cells in mice can be engineered to express a bioluminescent probe, which can be imaged to show how large the cancers grow, and where it can be located in the animal. While currently there are optical imaging tools that can perform two-dimensional ("2D") and three-dimensional ("3D") imaging, no information about the biological significance can be determined. For example, current imaging technologies can provide outputs in physical terms (e.g., photons per sec per $cm^2$), which does not provide information on the biological relevance.

While 2D or planar optical imaging of fluorescence or bioluminescence reporters has been performed in pre-clinical optical imaging, it can only provide relative light intensities at the tissue surface of the animal, which can be dependent on animal size, reporter probe location and imaging time point. Furthermore, a 3D reconstruction of such a light emitting source inside the tissue can provide the light emission density at the origin of light production. However, in 2D and 3D optical imaging, only a physical quantity with physical units (e.g., photons per sec per $cm^2$ or photons per sec per $cm^3$) can be available. Additionally, the physical quantity can often be expressed in relative terms (e.g. fold-changes) with respect to an initial study point. However, currently, there is no information about the actual quantity of biological relevance (e.g., amount of light emitting cancer cells, amount of light-emitting bacteria) that can directly relate to the biological target. In addition, no anatomical reference is currently available.

Thus, it may be beneficial to provide exemplary systems, methods and computer-accessible mediums that can provide fully quantitative information of anatomical structures (e.g., including small animals), that can determine the efficacy of one or more drugs, and which can overcome at least some of the deficiencies described herein above.

SUMMARY OF EXEMPLARY EMBODIMENTS

These and other objects of the present disclosure can be achieved by provision of exemplary systems, methods and computer accessible mediums which can determine quantitative information of a tissue(s), which can include receiving optical information regarding the tissue(s), and determining the quantitative information of the tissue(s), in real time and during the receipt of the optical information, using an anatomical atlas. The tissue(s) can be part of a mouse, and the quantitative information can be an in-vivo count of cells or bacteria in the tissue(s). The in-vivo count of the bacteria can be a lux-bacteria count. The lux-bacteria count can be determined using bioluminescence tomography and/or based on a calibration protocol.

The quantitative information can be determined by co-registering the in-vivo count to the atlas. The optical information can be generated using a mirror gantry(s) so as to simultaneously image at least two opposing views of the tissue(s). The two opposing views can be a dorsal view and a ventral view or a lateral left view and a lateral right view.

In some exemplary embodiments of the present disclosure, the optical information can be generated using an optically transparent mold(s) conforming to a body shape of the tissue(s). The atlas can include an organ probability map(s). In some exemplary embodiments of the present disclosure, the optical information can include a multispectral image(s) of bioluminescence light at a surface of the tissue(s). A map, which can be a three-dimensional map, of a luminescence of tissue(s) can be generated based on the quantitative information. The quantitative information can be determined based on a calibration protocol. An image of the tissue(s) can be generated based on the quantitative information. In certain exemplary embodiments of the present disclosure. the quantitative information includes information pertaining to a pathogenic bacterial infection.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION OF EXEMPLARY EMBODIMENTS

The exemplary systems, methods and computer-accessible mediums, according to an exemplary embodiment of the present disclosure, can measure drug efficacy and disease progression, in vivo, without having to sacrifice an animal. The exemplary systems, methods and computer-accessible mediums, according to an exemplary embodiment of the present disclosure, can derive quantitative information about the reporter in the cell (e.g., number of cells expressing bioluminescent probe), and can utilize a system to map the luminescence to a 3D map of the animal. The exemplary systems, methods and computer-accessible mediums, according to an exemplary embodiment of the present disclosure, can provide more precise information about a desired reporter than existing techniques. For example, a digital mouse atlas (e.g., anatomical reference) can be provided in real time, without the need for an auxiliary imaging modality, for example, magnetic resonance imaging ("MRI") or X-ray computerized tomography ("CT"). This can facilitate drug development by providing quantitative information about optical reporter systems.

The exemplary systems, methods and computer-accessible mediums, according to an exemplary embodiment of the present disclosure, can directly determine the absolute in vivo count of, for example, luminescing cancer cells or bacteria instead of using physical quantities relative to a single study time point. Furthermore, the in vivo cell count can be co-registered to a 3D organ probability map (e.g., a digital mouse atlas), which can directly conform to the animal's surface geometry defined by an exemplary animal mold.

The exemplary quantitative imaging unit/arrangement/system can include certain exemplary parts, for example: (1) a mirror gantry (e.g., mirror gantry 305 of FIG. 3) for simultaneously optical imaging of two opposing views (e.g., dorsal vs. ventral; lateral left vs. lateral right); (2) an optically transparent body-shape-conforming animal mold, which can constrain the animal to a defined spatial position; (3) an in vitro calibration cell for holding a known amount of luminescent cells; and (4) a digital mouse atlas that can represent an organ probability map. The exemplary imaging unit/arrangement/system can be placed in commercially available small animal optical imaging systems. The exemplary recorded imaging data can be processed by exemplary 3D image reconstruction software. An exemplary calibration protocol, which can utilize the calibration cell, can transform the processed physical quantities into biologically relevant quantities. The exemplary results, for example, the spatial in vivo distribution of luminescing cells, can be co-registered to the organ probability map while providing an anatomical reference.

Figure 3:
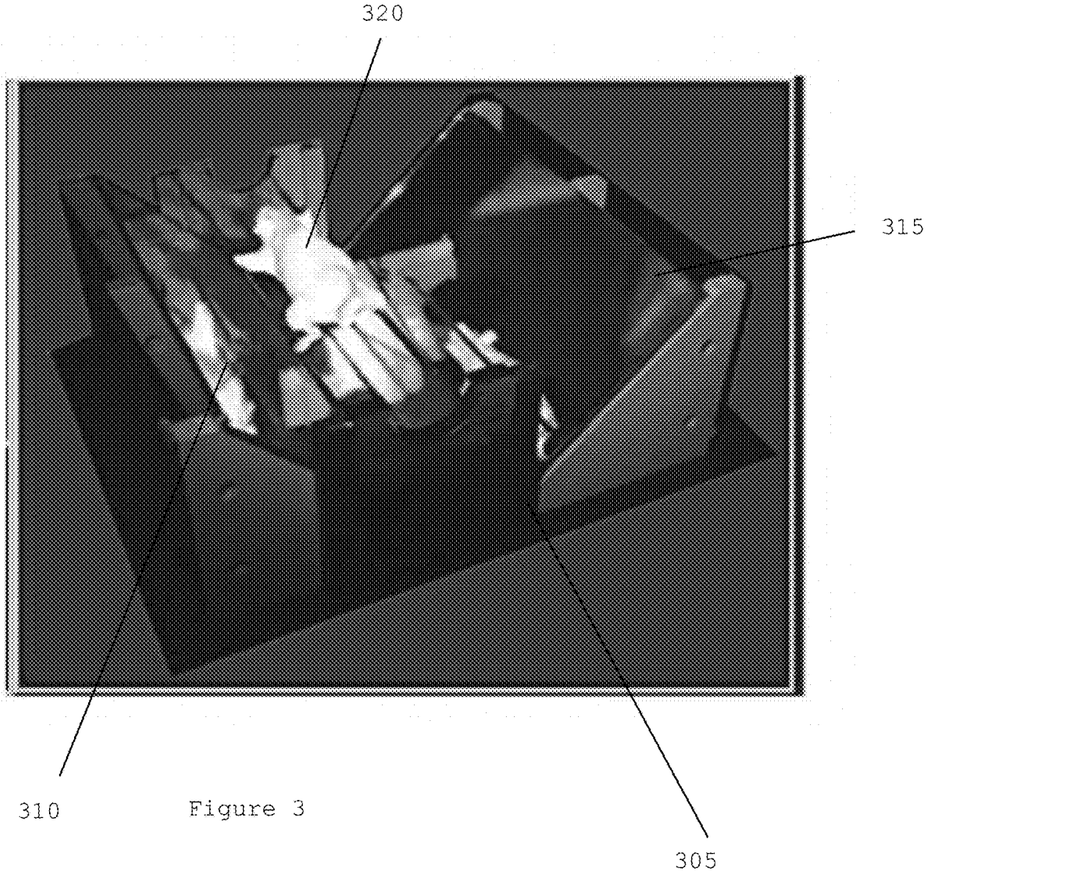
FIG. 3 is an exemplary image of an exemplary mirror gantry according to an exemplary embodiment of the present disclosure.

Mirror gantry 305 can consist of two optical mirrors (e.g., mirrors 310 and 315), which can facilitate simultaneous optical imaging of two different views of the animal mold. The exemplary two-part animal mold can consist of an optically transparent, but solid, material (e.g., polycarbonate) with the function of slightly compressing the animal 320 into the two shell-like mold pieces. Thus, the animal can have a fixed posture (e.g., constrained by the mold), and its tissue surface can be in light contact to the inner surface of the shell-like pieces. Both mold pieces can have the predefined curvature of a given mouse strain, gender and weight. The animal can be imaged while being inside the mold. The digital mouse atlas can provide an anatomical reference to the imaged animal.

This exemplary atlas can be developed from MRI or CT scans using a statistically sufficient amount of animals placed inside the mold. The exemplary images can be segmented for each animal, and an organ probability map (e.g., values between 0 and 1) can be derived from all animals by averaging over all segmented organs. For example, a voxel value of 1 can show the highest probability that a given organ can be present at the voxel location. A voxel value of 0 can show the highest probability that a given organ may not be present at the voxel location. The exemplary animal mold can facilitate the imaged animal and the mouse atlas to be spatially aligned.

Furthermore, the exemplary organ probability map can provide the basis for deriving a non-uniform optical tissue parameter map, which can include 'a priori' information for an ill-posed image reconstruction problem, for the exemplary 3D image reconstruction and quantification process. The exemplary calibration cell can be used for translating the 3D image reconstructions representing a physical quantity (e.g., light emission density) into a map of a biologically relevant and absolute quantity (e.g., absolute amount of light-emitting cells). The exemplary calibration cell (e.g., the optical calibrator) can consist of, or can include, a synthetic material which can have similar optical properties to the mouse (e.g., a mixture of resin and titanium-oxide nanospheres), and which can mimic biological tissue with exemplary optical tissue parameters as a function of the bioluminescence spectrum (e.g., between about 500 nm and about 800 nm). The solid calibration cell can have several small holes for holding in vitro samples (e.g., between about 10 and about 100 microliters) of known amounts of luminescent cells and, thus, can serve as calibration point for the 3D in vivo images.

The exemplary calibration cell can have four or more compartments with different absorption and scattering coefficients at a single wavelength band (e.g., centered at about 700 nm), with each compartment being equivalent to the optical properties of tissue at a single spectral band of about 50 nm between about 550 nm-about 720 nm of the bioluminescence spectrum. The exemplary image reconstruction procedure can utilize the optical images of the different compartments at a single wavelength band for reconstructing the light source of the luminescent cells inside the compartment holes.

Figure 1:
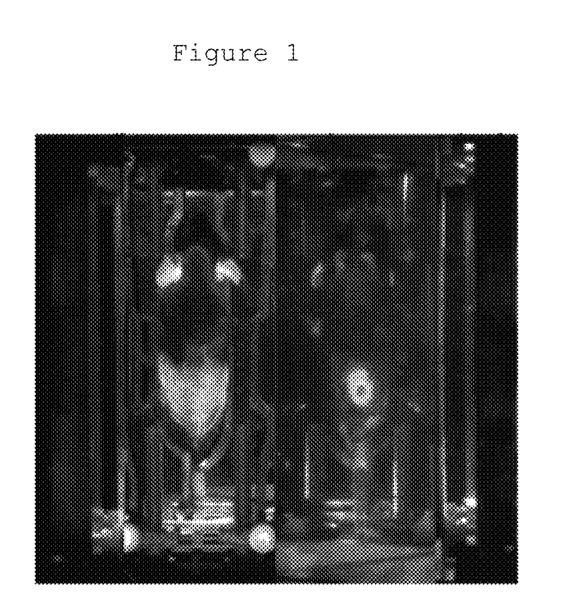
FIG. 1 is an exemplary image of a 50 ul of UPEC-lux (e.g., 3×10$^6$ bacteria) acquired without filter for 1 minute according to an exemplary embodiment of the present disclosure.
Figure 2:
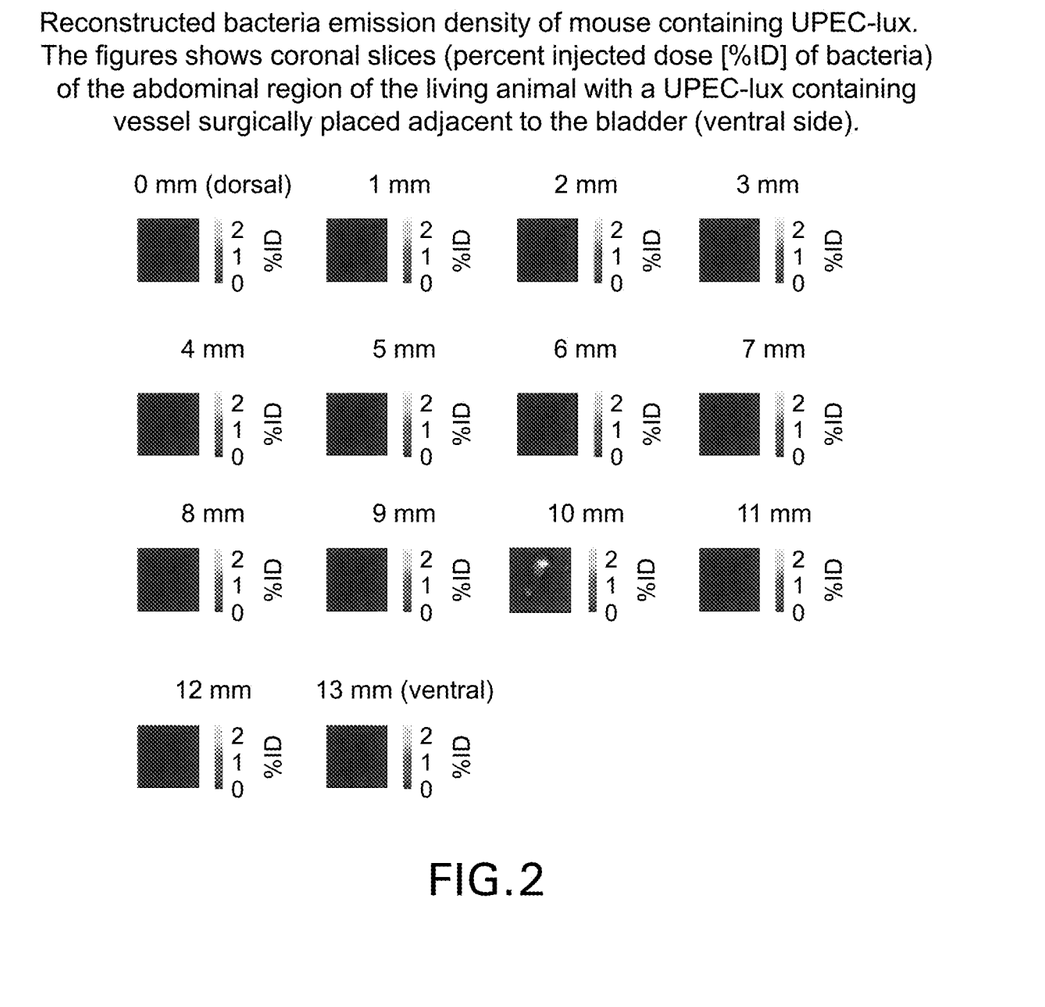
FIG. 2 is a set of exemplary images of reconstructed bacteria emission density of a mouse containing UPEC-lux according to an exemplary embodiment of the present disclosure.

The exemplary systems, methods and computer-accessible mediums, according to an exemplary embodiment of the present disclosure can quantify a pathogenic bacterial infection with the multispectral bioluminescence tomography ("BLT") of a bioluminescent uropathogenic *E. coli* ("UPEC-lux"). UPEC-lux can be generated by delivering the mini-Tn5-luxCDABE transposon to a clinical UPEC isolate (e.g., CFT073, ATCC 700928) by conjugation with the donor strain *E. coli* S17-1λ-pir (e.g., pUTmini-Tn5-luxCDABE-km2). The acute cystitis can be modeled by implanting a vessel with 50 µl of the UPEC-lux (e.g., FIG. 1). The in vivo lux-bacteria count can be calculated by employing BLT, and a calibration protocol for quantitative in vivo imaging. As an initial matter, the bioluminescence images can be acquired with a PhotonImager (e.g., BiospaceLab, France) at four different spectral windows centered at, for example, about 575, 615, 655, 695 nm and with an exemplary bandwidth of about 50 nm. The PhotonImager can use an image intensified charged-coupled-devices ("CCD"), camera and a mirror gantry for simultaneous imaging of the dorsal and ventral view. The exemplary image data set can be corrected for the non-uniform lux spectrum and the time-dependent emission kinetics of the lux-bacteria. FIG. 2 is a set of exemplary images of reconstructed bacteria emission density of a mouse containing UPEC-lux. Coronal slices can be seen (percent injected does [% ID] of bacteria) of the abdominal region of a living animal with a UPEC-lux containing vessel surgically placed adjacent to the bladder (e.g., ventral side).

A number of animals can be used for a pilot imaging study. One animal can be used for calibrating the unknown in vivo bacteria count. The animal can be anesthetized, and a 50 uL vessel with a known amount of bacteria can be implanted adjacent to the animal's bladder. The animal can be secured into an imaging cassette and placed onto the mirror gantry. Exemplary spectral images can be acquired at about a 3 minute camera integration time. The light intensity imaging data can be an input to an exemplary BLT reconstruction procedure based on an exemplary expectation-maximization ("EM") procedure and the simplified spherical harmonics ("SPN") equations for modeling in vivo light propagation. The exemplary EM procedure can reconstruct the 3D photon emission density of the lux bacteria. Post reconstruction, the total photon emission density of a volume of interest ("VOI") can be calculated and calibrated by using a known amount of bacteria placed in the vessel. The calculated in vivo bacteria count can be compared to the a priori known bacteria count, and agreement can be found between the calculated and given quantities (e.g., Pearson correlation coefficient $R2=0.98$). The UPEC-lux can be analyzed in a model of pyelonephritis, and the bacterial load in the kidney by BLT can be determined, which can correlate to CFUs from serial dilution of kidney homogenate. Thus, the unknown bacteria count can be determined inside a living animal.

Figure 4:
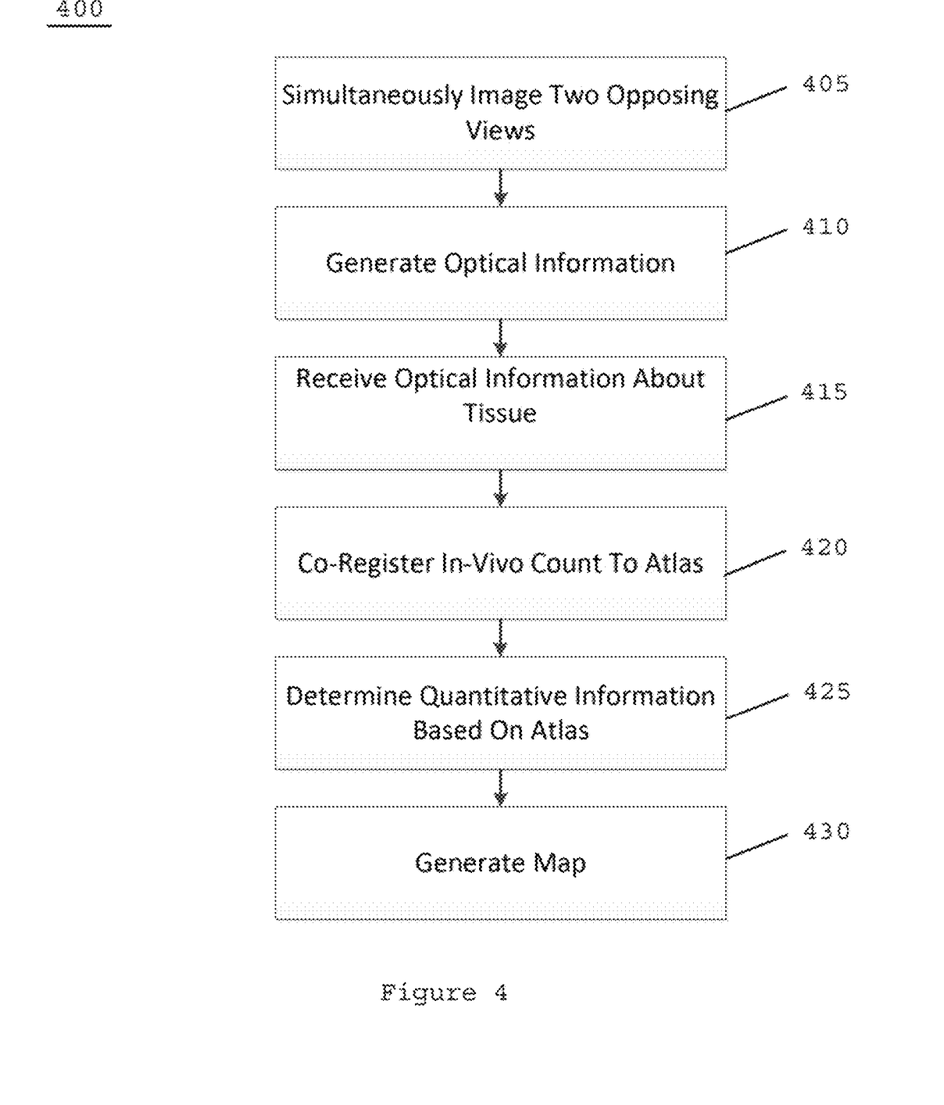
FIG. 4 is an exemplary flow diagram illustrating an exemplary method of determining quantitative information about a tissue according to an exemplary embodiment of the present disclosure.

FIG. 4 illustrates an exemplary method 400 for determining quantitative information. For example, at procedure 405, two opposing views of the tissue can be viewed for imaging. At procedure 410 the optical information about the tissue can be generated based on the two opposing views, which can be received at procedure 415. Alternatively, method 400 can begin at procedure 415 with the receipt of the optical information about the tissue. At procedure 420, and in-vivo count of the atlas can be co-registered. At procedure 425 the quantitative information can be determined based on the atlas, which can optionally be used to generate a map at procedure 430.

Figure 5:
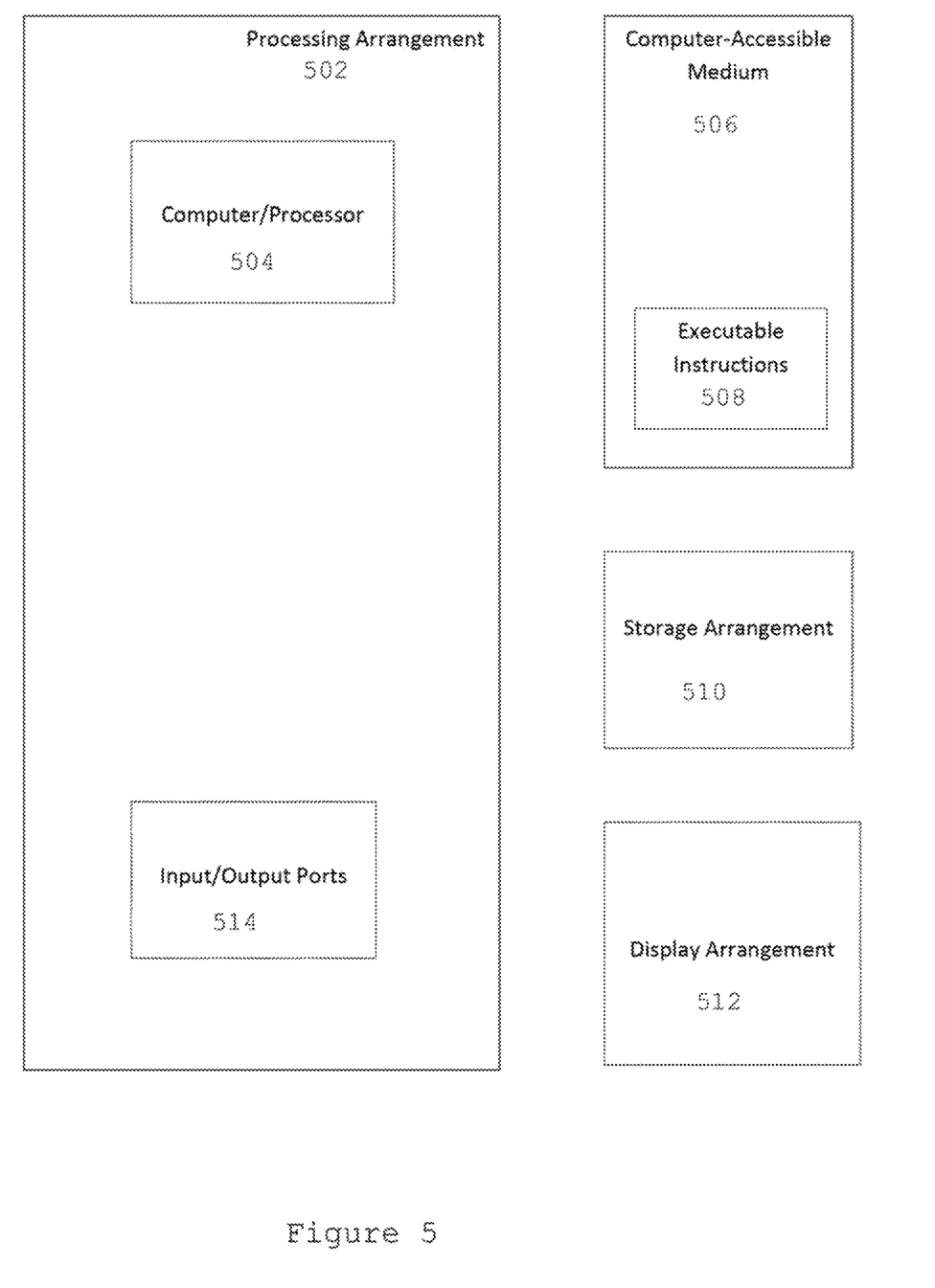
FIG. 5 is an illustration of an exemplary block diagram of an exemplary system in accordance with certain exemplary embodiments of the present disclosure.

FIG. 5 shows a block diagram of an exemplary embodiment of a system according to the present disclosure. For example, exemplary procedures in accordance with the present disclosure described herein can be performed by a processing arrangement and/or a computing arrangement 502. Such processing/computing arrangement 502 can be, for example, entirely or a part of, or include, but not limited to, a computer/processor 504 that can include, for example, one or more microprocessors, and use instructions stored on a computer-accessible medium (e.g., RAM, ROM, hard drive, or other storage device).

As shown in FIG. 5, for example, a computer-accessible medium 506 (e.g., as described herein above, a storage device such as a hard disk, floppy disk, memory stick, CD-ROM, RAM, ROM, etc., or a collection thereof) can be provided (e.g., in communication with the processing arrangement 502). The computer-accessible medium 506 can contain executable instructions 508 thereon. In addition or alternatively, a storage arrangement 510 can be provided separately from the computer-accessible medium 506, which can provide the instructions to the processing arrangement 502 so as to configure the processing arrangement to execute certain exemplary procedures, processes and methods, as described herein above, for example.

Further, the exemplary processing arrangement 502 can be provided with or include an input/output arrangement 514, which can include, for example, a wired network, a wireless network, the internet, an intranet, a data collection probe, a sensor, etc. As shown in FIG. 5 the exemplary processing arrangement 502 can be in communication with an exemplary display arrangement 512, which, according to certain exemplary embodiments of the present disclosure, can be a touch-screen configured for inputting information to the processing arrangement in addition to outputting information from the processing arrangement, for example. Further, the exemplary display 512 and/or a storage arrangement 510 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A method for determining quantitative information of at least one tissue, comprising:
   generating optical information regarding the at least one tissue based on at least one optically transparent mold conforming to a body shape of the at least one tissue;
   aligning the optical information to at least one digital atlas; and
   using instructions executed by a computer hardware arrangement, determining the quantitative information of the at least one tissue based on the aligned optical information.

2. The method of claim 1, wherein the at least one tissue is at least one part of a mouse, and further comprising placing the mouse in the at least one optically transparent mold.

3. The method of claim 2, further comprising generating an image of the at least one part of the mouse.

4. The method of claim 1, wherein the at least one tissue is part of a mouse.

5. The method of claim 1, wherein the quantitative information is an in-vivo count of at least one of cells or bacteria in the at least one tissue.

6. The method of claim 5, wherein the in-vivo count of the bacteria is a lux-bacteria count.

7. The method of claim 6, further comprising determining the lux-bacteria count using bioluminescence tomography.

8. The method of claim 6, further comprising determining the lux-bacteria count based on a calibration cell.

9. The method of claim 5, further comprising using the instructions executed by the computer hardware arrangement to determine the quantitative information by co-registering an in-vivo distribution of the at least one of the cells or the bacteria to the at least one digital atlas.

10. The method of claim 4, wherein the at least one digital atlas is at least one digital mouse atlas.

11. The method of claim 10, wherein the at least one digital mouse atlas includes at least one organ probability map, and wherein the at least one organ probability map is a statistical representation of a plurality of digital mouse atlases.

12. The method of claim 11, wherein the at least one organ probability map is a three-dimensional organ probability map.

13. The method of claim 1, further comprising generating a map of a luminescence of the at least one tissue based on the quantitative information.

14. The method of claim 13, wherein the map is a three-dimensional map.

15. The method of claim 14, further comprising using the instructions executed by the computer hardware arrangement to determine the quantitative information based on a calibration cell.

16. The method of claim 1, further comprising generating an image of the at least one tissue based on the quantitative information.

17. The method of claim 1, wherein the quantitative information includes information pertaining to a pathogenic bacterial infection.

18. A system for determining quantitative information of at least one tissue, comprising:
   at least one optically transparent mold conforming to a body shape of the at least one tissue; and
   a computer hardware arrangement including instructions, which when executed by the computer hardware arrangement:
      generate optical information regarding the at least one tissue based on the at least one optically transparent mold;
      align the optical information to at least one digital atlas; and
      determine the quantitative information of the at least one tissue based on the aligned optical information.

19. The system of claim 18, wherein the executed instructions are configured to be used by the computer hardware arrangement to generate a map of a luminescence of the at least one tissue based on the quantitative information.

20. The system of claim 19, wherein the map is a three-dimensional map, and wherein the executed instructions are configured to be used by the computer hardware arrangement to determine the quantitative information based on a calibration cell.

21. A method for determining quantitative information of at least one tissue, comprising:
   generating optical information regarding the at least one tissue based on at least one optically transparent mold conforming to a body shape of the at least one tissue;
   aligning the optical information to at least one organ probability map, wherein the at least one organ probability map is a statistical representation of a plurality of digital mice atlases; and
   using instructions executed by a computer hardware arrangement, determining the quantitative information of the at least one tissue based on the aligned optical information.

22. The method of claim 21, wherein the at least one organ probability map is a three-dimensional organ probability map.

* * * * *